(12) United States Patent
Scharnberg et al.

(10) Patent No.: US 6,223,088 B1
(45) Date of Patent: Apr. 24, 2001

(54) ELECTRODE AND CONNECTOR ASSEMBLY AND METHOD FOR USING SAME

(75) Inventors: Lorne C. Scharnberg, Des Moines, IA (US); Warren R. Walters, Lakeville, MN (US); William L. Heard II, Clive; William A. Todd, Jr., Indianola, both of IA (US)

(73) Assignee: Katecho, Incorporated, Des Moines, IA (US)

( * ) Notice: Subject to any disclaimer, the term of this patent is extended or adjusted under 35 U.S.C. 154(b) by 0 days.

(21) Appl. No.: 09/188,617

(22) Filed: Nov. 9, 1998

(51) Int. Cl.[7] ........................................... A61N 1/04
(52) U.S. Cl. ................. 607/142; 439/909; 607/152; 600/372
(58) Field of Search ..................... 607/142, 149, 607/152, 153; 600/372, 386, 391, 392, 393; 439/789, 909

(56) References Cited

U.S. PATENT DOCUMENTS

| 4,072,388 | 2/1978 | Dunn . | |
|---|---|---|---|
| 4,126,126 | 11/1978 | Bare et al. . | |
| 4,635,642 | 1/1987 | Cartmell et al. . | |
| 4,702,256 | 10/1987 | Robinson et al. . | |
| 4,797,125 | * 1/1989 | Malana | 439/909 |
| 4,798,208 | * 1/1989 | Fasse, Jr. | 600/392 |
| 4,974,594 | * 12/1990 | Berlin | 600/395 |
| 5,195,523 | * 3/1993 | Cartmell et al. | 439/909 |
| 5,407,368 | * 4/1995 | Strand et al. | 439/909 |
| 5,520,683 | * 5/1996 | Subramaniam et al. | 607/142 |
| 5,916,244 | * 6/1999 | Walters | 607/142 |

* cited by examiner

*Primary Examiner*—Kennedy Schaetzle
(74) *Attorney, Agent, or Firm*—Zarley, McKee, Thomte, Voorhees & Sease

(57) ABSTRACT

An electrode and connector are detachably connected to one another for use in defibrillating or pacing a patient's heart. The connector includes two jaw members which clamp over a tab portion of the electrode. The jaw members include electrical contacts which engage and contact the conductive sheet within the electrode. This provides electrical continuity from the electrode through the connector to a lead wire.

10 Claims, 5 Drawing Sheets

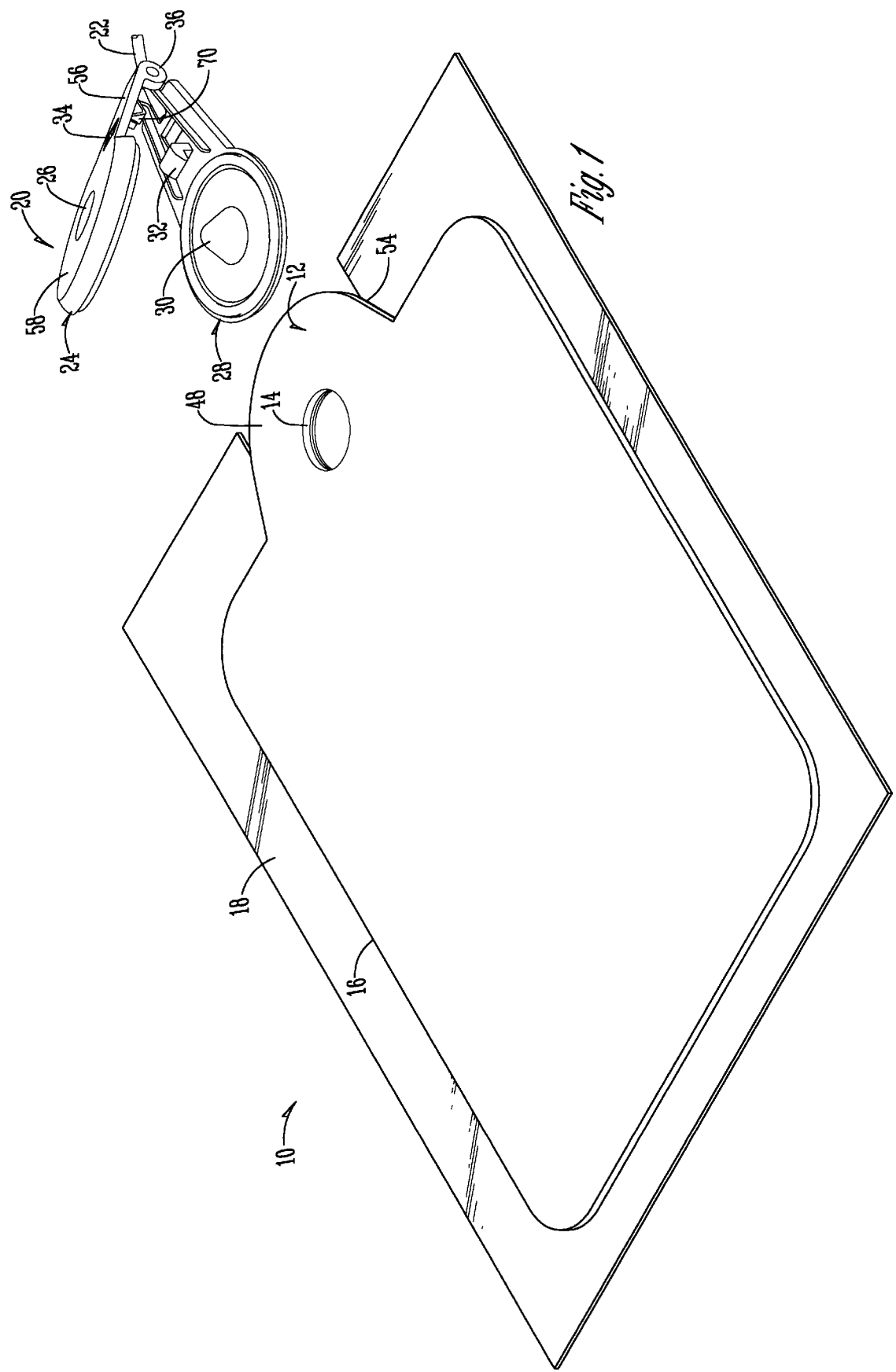

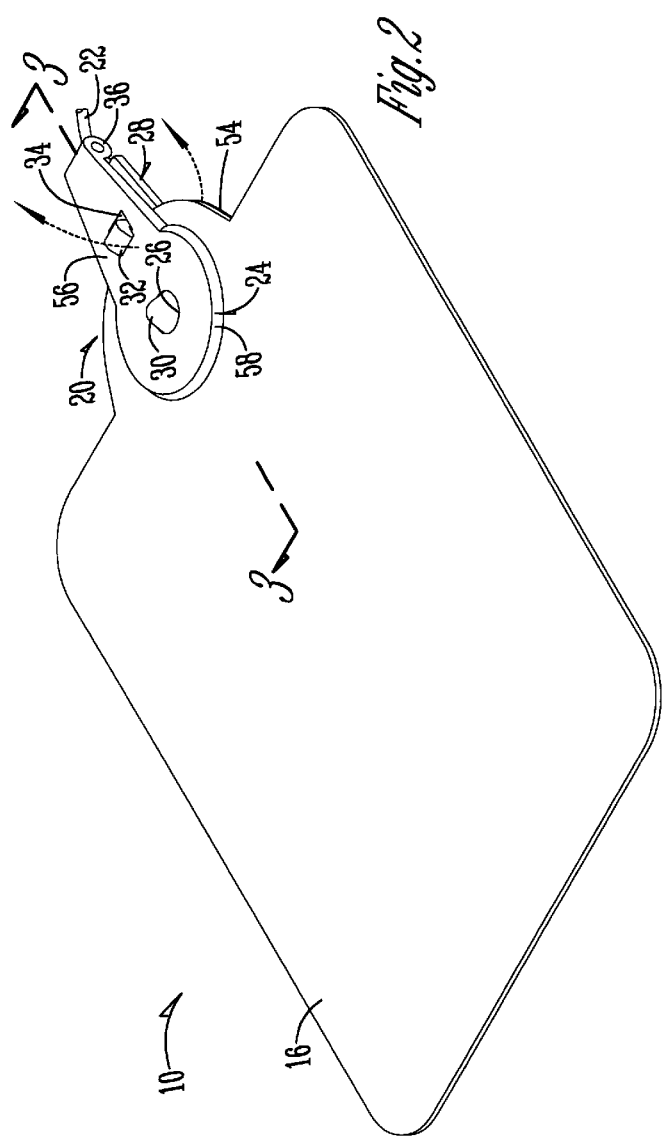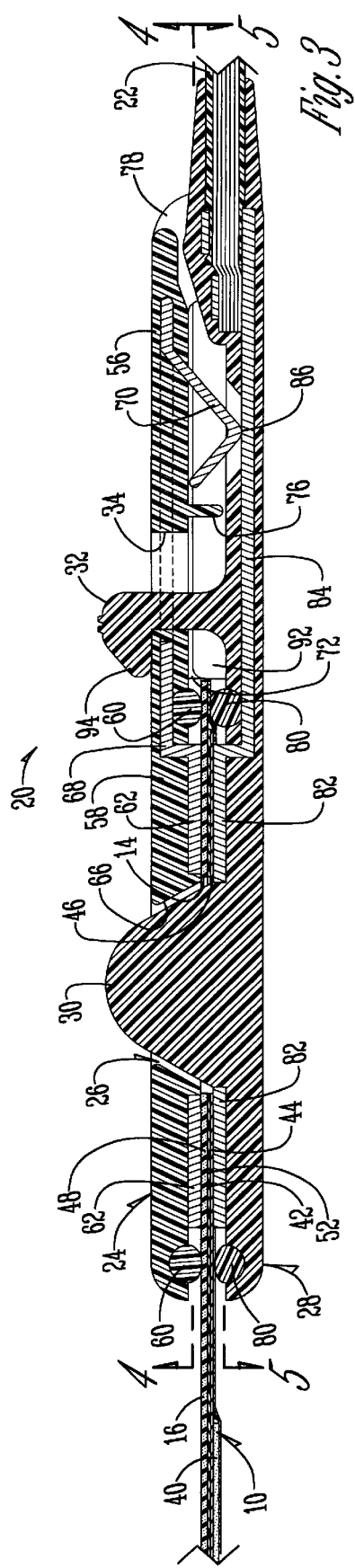

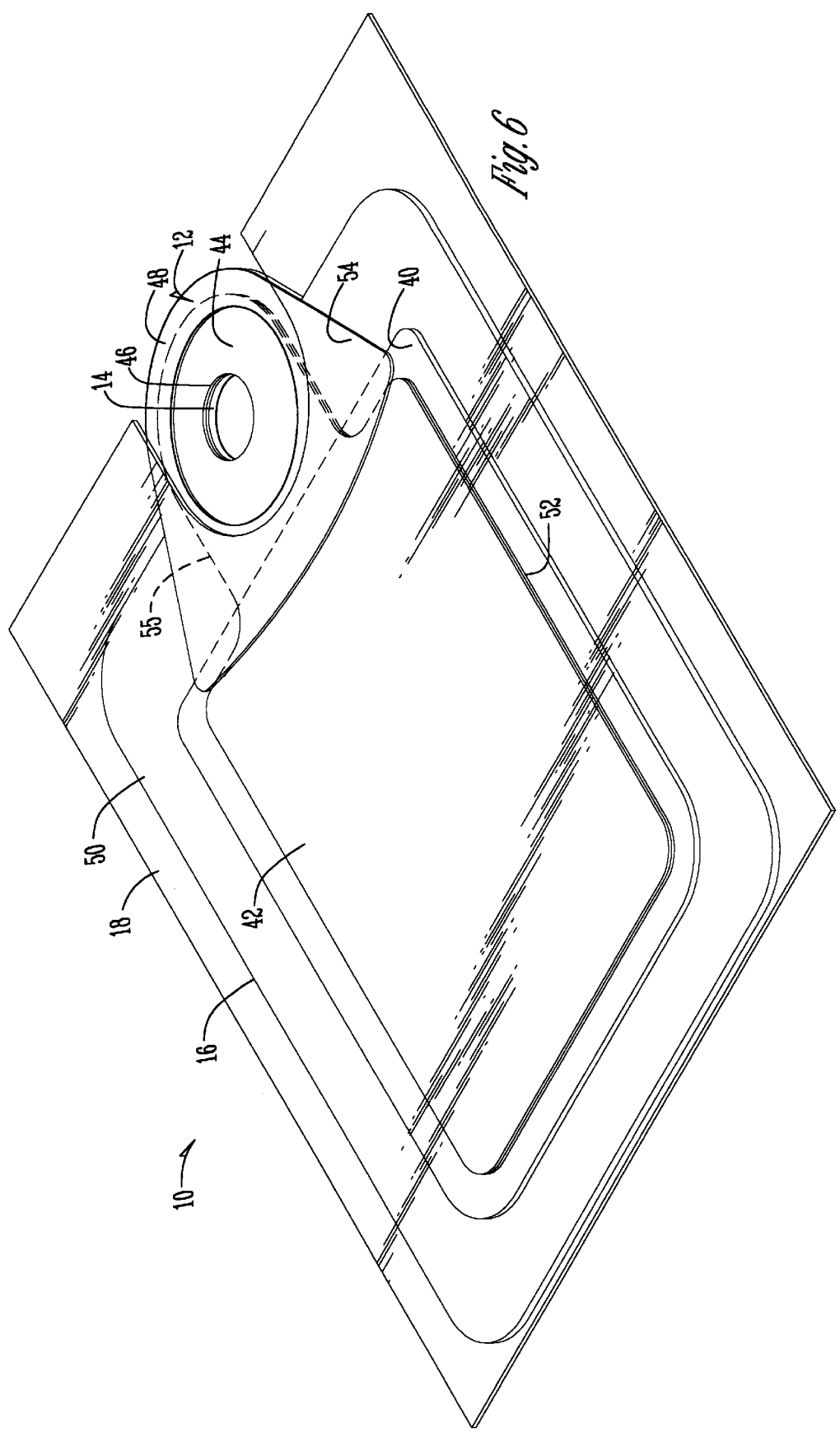

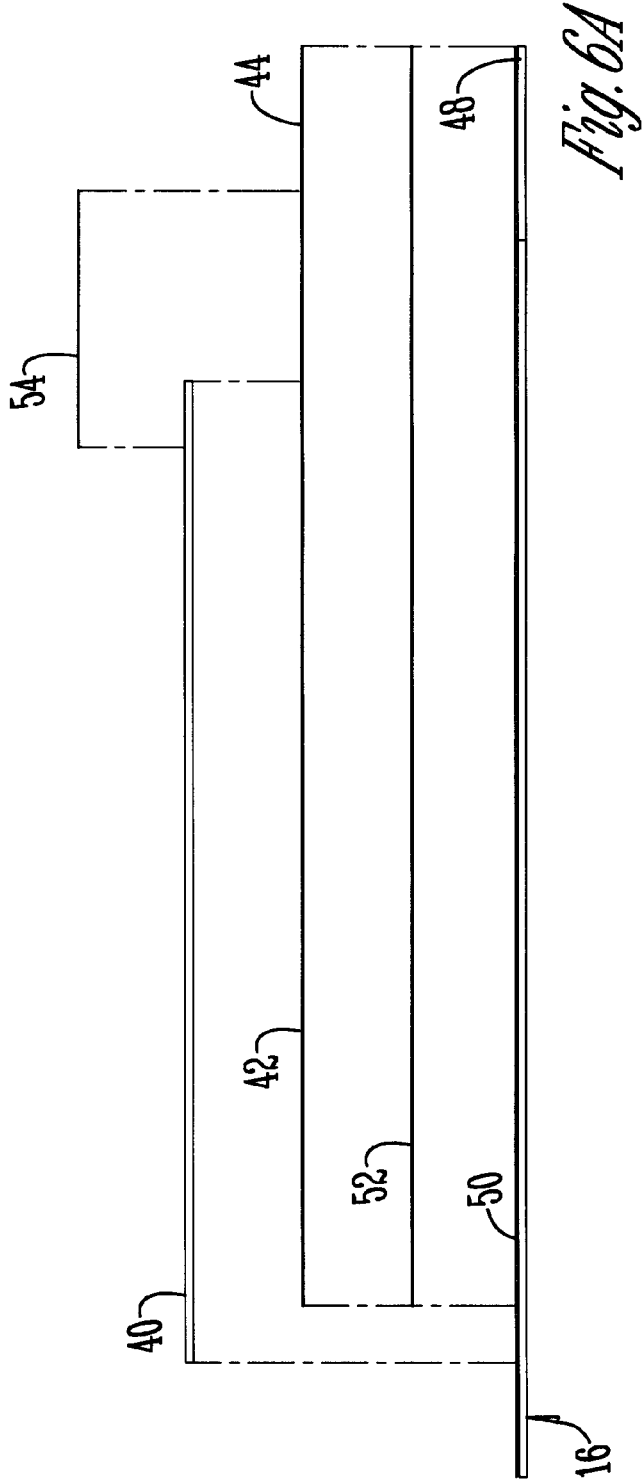

ELECTRODE AND CONNECTOR ASSEMBLY AND METHOD FOR USING SAME

BACKGROUND OF THE INVENTION

The present invention relates to an electrode and connector assembly and method for using same.

More particularly the present invention relates to electrodes used for external pacing, defibrillation, and monitoring of the heart. Often these electrodes have multiple functions. Some are used for defibrillation, pacing, and monitoring. Others are used for pacing only. Still others are used for defibrillation and monitoring. These electrodes are usually substantially larger than other types of electrodes, such as electrodes used solely for monitoring. The larger size is necessary because of the need to spread large electrical charges used for defibrillating or pacing over a larger surface than would be needed for an electrode used solely for monitoring.

In the defibrillation process a charge of electricity is introduced to the patient through the external electrode for stimulating the heart and for correcting heart fibrillation. For pacing a charge is introduced to the patient through the electrode for pacing the heartbeat.

Electrodes used only for monitoring receive small quantities of electrical energy generated when the patient's heart beats. These small quantities of electricity are transmitted through the electrode to a console which is capable of analyzing and charting the patient's heartbeat.

Electrodes used for the above purposes are often disposable. They are placed on the patient's skin during use and then discarded. These disposable electrodes usually include electrical connectors or wires which are connected permanently to the electrode and which lead to a console or machine for performing the various functions intended. Disposal of these electrodes also results in the disposal of the connectors or the wires because the connectors or wires are usually permanently connected to the electrode.

The connectors and the wires are the most expensive components of prior art defibrillation and pacing electrodes. Disposal of the connectors and/or the wires with the electrodes results in wasted cost.

One solution to this waste problem is to provide a defibrillation or pacing electrode that can be detached from the connector and wire before disposal. There are several problems however in providing a detachable connector to an electrode used for defibrillation or pacing. The connector must provide positive and reliable contact with the electrode so as to minimize arcing, failure, or any form of open circuit to the electrode during the defibrillation or pacing process.

The detachable connector must also be fail-safe. Paramedics or other medical personnel applying the electrodes to a patient are often doing so under conditions of emergency. Because of this, the connector must be one which can be attached quickly and easily with a minimum of confusion. The structure of the connector should be such that even under these confusing circumstances the medical personnel can attach the connector to the electrode in a reliable manner.

The connector must provide a strong connection to the electrode because often the conditions under which the electrode is being used are conducive to jostling, moving, and other forms of physical movement between the connector and the electrode. The strength of the connection is therefore important to maintaining proper electrical continuity.

Therefore, a primary object of the present invention is the provision of an improved electrode and connector assembly and method for using same.

A further object of the present invention is the provision of an electrode that can be used for defibrillation or pacing but which does not have a connector or wire permanently attached to the electrode.

A further object of the present invention is the provision of an electrode and connector assembly for use in defibrillation or pacing and which permits the electrode to be disposable without having to dispose of the connector or the wire.

A further object of the present invention is the provision of an improved electrode and connector assembly for use in defibrillation or pacing and which provides detachable connection between the connector and the electrode.

A further object of the present invention is the provision of an electrode and connector assembly which provides detachable, but also very strong and reliable connection between the connector and the electrode.

A further object of the present invention is the provision of an improved electrode and connector assembly which will function even if the medical personnel attach the connector in a reverse position from its intended connection.

A further object of the present invention is the provision of an electrode and connector assembly which includes a connector that can be quickly and easily attached during confusing circumstances often encountered in a medical emergency.

A further object of the present invention is the provision of an improved electrode and connector assembly which is economical to manufacture, durable in use, and efficient in operation.

SUMMARY OF THE INVENTION

The foregoing objects may be achieved by a combination of an electrode for defibrillation or pacing and a detachable connector. The electrode includes a dielectric backing layer, a conductive sheet layer, and a conductive gel layer. The conductive sheet layer includes a tab portion. An electrically conductive wire includes first and second opposite ends and a connector connected to the first end of the wire. The connector is detachably connected to the tab portion of the conductive sheet layer on the electrode. The connector has a first electrical contact providing electrical continuity between the tab portion of the conductive layer of the electrode and the conductor wire.

The tab portion of the conductive layer includes a hole extending therethrough and the connector includes a post protruding through the hole in the tab portion.

The electrode itself contains no connector or wire. This substantially reduces the cost of the electrode and consequently makes disposal of the electrode less expensive. The connector and wire may be used over and over again with different electrodes.

The connector includes first and second jaw members embracing the tab portion of the conductive sheet layer therebetween, and a post extends from the first of these members. The second member includes a hole extending therethrough and the post protrudes at least partially through the hole in the second member.

In use, the jaw members of the connector are positioned over the tab portion of the electrode. The jaws are clamped together over the tab potion of the electrode, with the post of one of the jaw members protruding through the hole in the tab portion and also through the hole in the other jaw member. A latch latches the two jaw members together in a clamped position over the tab portion of the electrode. In this position the connector is tightly secured to the tab portion and cannot be removed due to the post extending through the hole in the tab portion.

Each of the jaw members includes its own respective electrical contact leading to the wire, so that the connector can be attached over the tab portion of the electrode in a reverse position from its usual intended position, and still function as a proper connector to the wire. The connector and electrode assembly are very reliable and provide strong structural and electrical connection between the wire and the electrode. After use, the connector can be detached from the tab portion of the electrode and the electrode may be thrown away.

The present invention is preferred for use in defibrillating or pacing, but may have application for use in other types of electrode functions.

BRIEF DESCRIPTION OF THE FIGURES OF THE DRAWINGS

FIG. 1 is a perspective view of the electrode and connector assembly of the present invention.

FIG. 2 is a view similar to FIG. 1, but showing the release liner removed from the electrode and showing the connector in its clamped position attached to the electrode.

FIG. 3 is a sectional view taken along line 3—3 of FIG. 2.

FIG. 6 is a bottom perspective view of the electrode of the present invention.

FIG. 6A is a schematic view of the various layers within the electrode.

DETAILED DESCRIPTION OF THE PREFERRED EMBODIMENT

Figure 4:
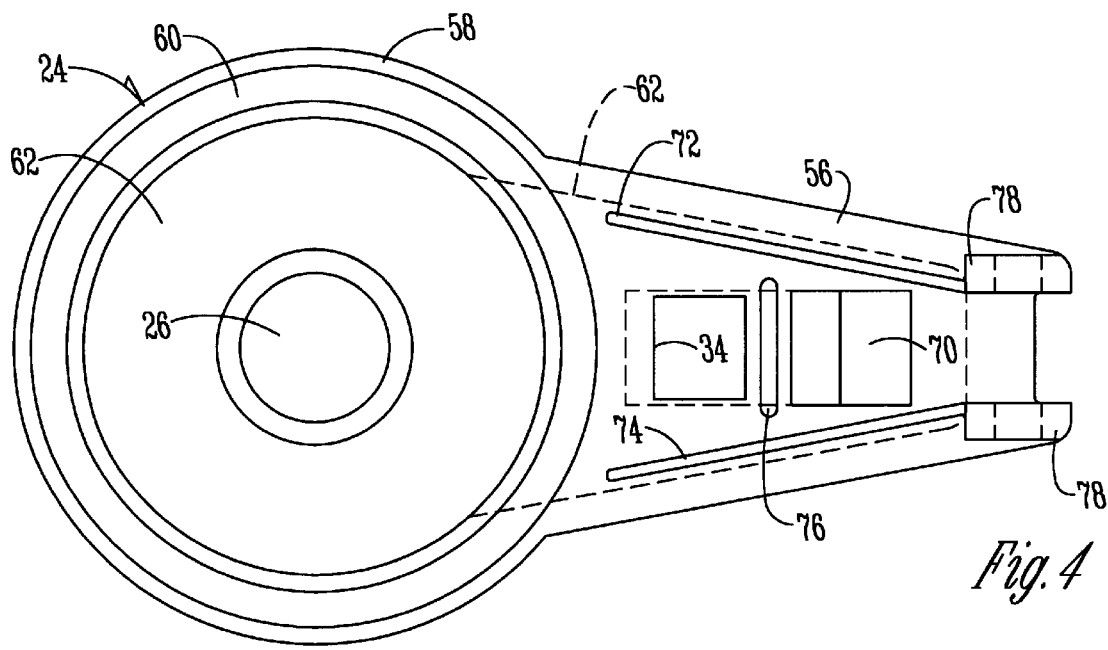
FIG. 4 is a sectional view taken along line 4—4 of FIG. 3.
Figure 5:
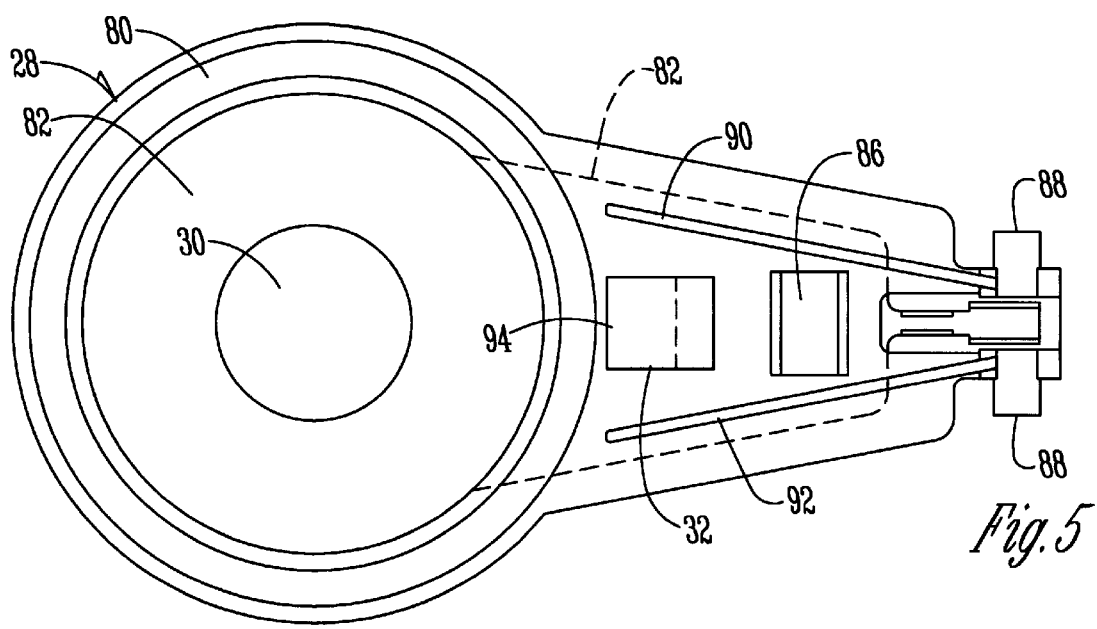
FIG. 5 is a sectional view taken along line 5—5 of FIG. 3.

Referring to FIGS. 1 and 2 an electrode 10 includes a tab 12 having a hole 14 extending therethrough. The electrode 10 includes a backing layer 16 which is made of a dielectric material and a release liner 18 which is removed from the electrode during use.

The specific structure of the electrode 10 is shown in FIGS. 6 and 6A. Closest to the patient is a hydrogel or conductive adhesive layer 40 which is commonly used for electrodes of this type. The hydrogel 40 is tacky and is adapted to attach to the patient's skin. The hydrogel 40 is also electrically conductive. Examples of hydrogels which may be used for this purpose are a gel manufactured by LecTec Corporation under the product designation LT3300. Another example is a gel manufactured by Ludlow Corporation under the product designation RG63T.

Immediately below the hydrogel 40 is a conductive sheet 42. Conductive sheet 42 may be tin, carbon, or a carbonized polymer material commonly used for electrodes of this type. It is a highly conductive material so that it will provide electrical continuity from the patient's chest through the hydrogel layer 40 and through the conductive sheet 42. Below the conductive sheet 42 is a reinforcing or strengthening layer 52. A preferred material for the strengthening layer 52 is a material manufactured by DuPont under the trademark Tyvec®. It is a dielectric spunbonded olefin material which imparts strength to the conductive sheet 42. The electrode may be manufactured without the strengthening layer 52, but it is preferred that the strengthening layer 52 be utilized. Below the strengthening layer 42 is the backing sheet 16.

The conductive sheet 42 includes a tab portion 44 having a hole 46 extending therethrough. Hole 46 is registered with hole 14 in the backing layer 16. The backing sheet layer 16 is a dielectric material and includes a backing sheet tab 48 (FIG. 1) which is registered with the tab portion 44 of the conductive sheet 42. The upper surface of sheet 16 as viewed in FIG. 6A includes an adhesive coating 50 thereon for attaching to the strengthening layer 52 and the conductive sheet 42. Adhesive 50 also facilitates attachment of electrode 10 to a patient's skin. The sheets 40, 42, 52, and 16 are all assembled in a laminated fashion.

As can be seen in FIG. 6, the upper surface of tab portion 44 of conductive sheet 42 is exposed. A front pad 54 which is dielectric covers the neck portion 55 of the conductive layer 42, but leaves the tab portion 44 exposed.

FIG. 1 shows the proper orientation of electrode 10 for placement on a patient's chest. The exposed portion of tab 44 is presented downwardly, and the tab 12 of the backing layer 16 is presented upwardly.

A connector 20 is permanently connected to a lead wire 22 and includes an upper jaw member 24, having a shank portion 56 and a rounded portion 58. A hole 26 extends through the rounded portion 58 of the upper jaw member 24. Connector 20 also includes a lower jaw member 28 having an upwardly protruding post 30, which when clamped in the position shown in FIG. 2 protrudes through hole 14 in backing sheet 16, hole 46 in conductive sheet 42, and at least partially through hole 26 in the upper jaw member 24.

Referring to FIG. 3, the upper jaw member 24 includes a circular sealing ring 60 which surrounds an upper contact 62. Upper contact 62 is flat much in the shape of a washer and surrounds hole 26 in upper jaw member 24. The hole 26 includes tapered margins 66 which permit the post or nose 30 to cam upwardly during the closing of the upper and lower jaw members 24, 28 with respect to one another.

Embedded within the upper jaw member 24 is an embedded contact 68 which is in electrical connection with upper contact 62 and which extends rearwardly within upper jaw member 24 until it protrudes outwardly from jaw member 24 to form a spring contact 70. Spring contact 70 engages the lower jaw member 28 and provides a spring action yieldably holding the jaw members 24, 28 spread apart from one another in the position shown in FIG. 1.

Upper jaw member 24 includes two elongated shield side ribs 72, 74 (FIG. 4) which shield the spring 70 and prevent sparks from exiting the connector 20 during use. A shield cross rib 76 provides the same function. At the rear of the upper jaw 24 are a pair of hinge bosses 78.

Bottom jaw member 28 includes a sealing ring 80 positioned to register with the sealing ring 60 of the upper jaw member 24. The sealing rings 60, 80 are sufficiently flexible to provide sealing contact with the electrode 10 when the jaw members 24, 28 are in their closed position.

Surrounding the nose or post 30 is a lower contact 82 which is in the shape of a washer and which corresponds generally to the size and shape of the upper contact 62. An embedded contact 84 is in electrical connection with the lower contact 82 and extends rearwardly to an exposed portion 86 which is in contact with spring 70. The embedded contact 84 then extends rearwardly and is in electrical contact with the wire 22. The rear of bottom jaw member 28 includes a pair of spaced apart hinge pins 88 which are adapted to fit within the hinge bosses 78 so as to provide a hinged connection between upper and lower jaw members 24, 28.

The upper surface of the lower jaw member 28 also includes shield side ribs 90, 92.

A latch mechanism is provided for latching the upper and lower jaw members 24, 28 in their closed positions and includes a latch member 32 having a latch pawl 94 thereon. latch member 32 is adapted to fit through a latch hole 34 extending through the upper jaw member 24.

In operation, the jaw members 24, 28 are normally held in their open position by the engagement between spring 70 and contact 86. In order to attach the connector 20 to the electrode 10, the nose or post 30 is inserted through the opening 14 and the jaw members 24, 28 are closed or clamped together, pivoting about the hinge 36 formed by hinge pins 38 and hinge bosses 78. The latch 32 extends through the opening 34 and the pawl 94 springs into engagement with the upper surface of the upper jaw member 24 so as to latch the two jaw members 24, 28 together in the position shown in FIGS. 2 and 3.

In this clamped position the lower contact 82 is in direct contact with the tab portion 44 of conductive sheet 42. This provides electrical continuity from the patient's skin, through the hydrogel 40, then through the conductive sheet member 42, then through the lower contact 82 and the embedded contact 84 to provide electrical continuity to the wire 22.

The various shield ribs 72, 74, 76, 90 and 92 prevent any inadvertent sparking from being emitted from the electrical connector 20.

The connector 20 is intended to be connected with the bottom contact 82 in contact with the electrical conductive sheet 42. However, in the confusion of an emergency situation it is possible that the operator may connect the connector 20 in a reverse position from its intended use so that the upper jaw member 24 is facing downwardly and the lower jaw member 28 is facing upwardly. In this situation the upper contact 62 will engage the conductive sheet member 42 and the embedded contact 68 will provide electrical connection through the spring 70 to the exposed portion 86 of the embedded conductor 84, and thence to the wire 22.

Thus the connector 20 provides a fail-safe function in the event that it is connected in an inverted or reversed manner. In such a situation it will still provide good electrical conductivity and continuity from the patient's skin to the wire 20.

The tapered surface 66 provides a camming action between the nose 30 and the upper jaw member 24 so that in the confusion and haste of an emergency situation the upper and lower jaw members will cam together and self-align to the proper position. The fact that the post 30 protrudes through the holes 14, 46 of the electrode 10 provides solid mechanical and electrical connection between the connector 20 and the electrode 10.

In the drawings and specification there has been set forth a preferred embodiment of the invention, and although specific terms are employed, these are used in a generic and descriptive sense only and not for purposes of limitation. Changes in the form and the proportion of parts as well as in the substitution of equivalents are contemplated as circumstances may suggest or render expedient without departing from the spirit or scope of the invention as further defined in the following claims.

What is claimed is:

1. In combination:
a defibrillation or pacing electrode comprising a dielectric backing layer, a conductive sheet layer, and a conductive gel layer;
the conductive sheet layer having a tab portion with an exposed tab contact, said tab portion and said exposed tab contact having a hole extending therethrough;
an electrically conductive wire having first and second opposite ends;
a connector having a first jaw member having an electrically conductive first jaw contact and a second jaw member having an electrically conductive second jaw contact, said jaw members being hinged together for hinged movement about a jaw axis from an open position wherein said first and second jaw contacts are spaced from one another to a closed position wherein said first and second jaw contacts are closely adjacent one another but free from engagement with one another;
the first and second jaw contacts being in electrical connection with said conductive wire when said first and second jaw members are in both said open position and in said closed position;
the first jaw member having a post thereon and the second jaw member having an opening therein;
the first and second jaw members being in said closed position embracing the tab portion therebetween with said post extending through the hole in the tab portion and at least partially through the opening in the second jaw member, and with at least one of said first jaw contact and the second jaw contact being in electrical contact with the exposed tab contact to create electrical continuity from the conductive sheet layer to the electrically conductive wire.

2. A combination according to claim 1 said one of said first and second jaw contacts is said first jaw contact.

3. A combination according to claim 1 wherein said one of said first and second jaw contacts is said second jaw contact.

4. A connector according to claim 1 wherein said first and second jaw members are reversible from a normal position wherein only said first jaw contact is in electrical contact with said exposed tab contact to a reversed position wherein only said second jaw contact is in electrical contact with said tab contact.

5. A connector for providing electrical connection between an electrical wire and a defibrillating or pacing electrode, said electrode comprising a dielectric backing layer, a conductive sheet layer, and a conductive gel layer; the conductive sheet layer having a tab portion with an exposed tab contact, said tab portion and said exposed tab contact having a hole extending therethrough; said connector comprising:
a first jaw member having an electrically conductive first jaw contact and a second jaw member having an electrically conductive second jaw contact, said jaw members being hinged together for hinged movement about a jaw axis from an open position to a closed position;
the first and second jaw contacts being in electrical connection with said conductive wire both when said first and second jaw members are in said open position and when said first and second jaw members are in said closed position;
the first jaw member having a post thereon and the second jaw member having an opening therein;

the first and second jaw members being movable to said closed position embracing the tab portion therebetween with said post extending through the hole in the tab portion and at least partially through the opening in the second jaw member, and with at least one of said first and second jaw contacts being in electrical contact with the exposed tab to create electrical continuity from the conductive sheet layer to the electrically conductive wire.

6. A connector according to claim 5 wherein said first and second jaw members are reversible from a normal position wherein only said first jaw contact is in electrical contact with said exposed tab contact to a reversed position wherein only said second jaw contact is in electrical contact with said exposed tab contact.

7. A method for connecting a defibrillation or pacing electrode to a lead wire, the electrode comprising a dielectric backing sheet, a conductor sheet, and a conductive adhesive sheet, the conductor sheet having a tab portion protruding from the electrode and having a first face, an opposite second face, and an exposed tab contact thereon, said method comprising:

taking a connector comprising a first jaw member having a first jaw contact and a second jaw member with a second jaw contact, said first and second jaw contacts being in electrical contact with said lead wire;

moving said first and second jaw members to an open position wherein said first and second jaw contacts are spaced from one another;

placing said tab portion between said first and second jaw contacts so that said first face of said tab portion faces said first jaw member and said second face of said tab portion faces said second jaw member when said first and second jaw members are in said open position;

moving said first and second jaw members to a locked position embracing said tab portion therebetween with at least one of said first and second jaw contacts in electrical contact with said tab contact to provide electrical continuity from said lead wire to said conductor sheet;

maintaining both of said first and second jaw contacts in electrical connection with said lead wire when said first and second jaw members are in both of said open and said locked positions placing said electrode on patient's chest and defibrillating or pacing said patient's heart.

8. A method according to claim 7 and further comprising reversing the position of said first and second jaw members during said placing step so that said first face of said tab portion faces said second jaw member and said second face of said tab faces said first jaw member.

9. A method according to claim 8 wherein said tab contact includes a tab contact hole extending therethrough, one of said first and second jaw contacts includes a jaw contact hole therein and the other of said first and second contacts includes a post thereon, said moving step further comprising moving said post through said tab contact hole and at least partially through said jaw contact hole to provide positive physical attachment of said connector to said electrode.

10. A method according to claim 7 wherein said tab contact includes a tab contact hole extending therethrough, one of said first and second jaw contacts includes a jaw contact hole therein and the other of said first and second contacts includes a post thereon, said moving step further comprising moving said post through said tab contact hole and at least partially through said jaw contact hole to provide positive physical attachment of said connector to said electrode.

* * * * *